(12) United States Patent
Blackman

(10) Patent No.: US 8,128,962 B2
(45) Date of Patent: Mar. 6, 2012

(54) LIQUID COMPOSITIONS CONTAINING SOLUBILIZED BENZOYL PEROXIDE, MEANS FOR APPLYING SAME AND METHODS OF TREATMENT USING SAME

(76) Inventor: Steven T Blackman, Boca Raton, FL (US)

( * ) Notice: Subject to any disclaimer, the term of this patent is extended or adjusted under 35 U.S.C. 154(b) by 114 days.

(21) Appl. No.: 12/773,322

(22) Filed: May 4, 2010

(65) Prior Publication Data

US 2010/0216888 A1     Aug. 26, 2010

Related U.S. Application Data

(62) Division of application No. 11/820,949, filed on Jun. 21, 2007, now Pat. No. 7,727,562.

(51) Int. Cl.
*A61K 33/40* (2006.01)
*A61K 36/534* (2006.01)

(52) U.S. Cl. ........................................ 424/613; 424/747

(58) Field of Classification Search .................... None
See application file for complete search history.

(56) References Cited

U.S. PATENT DOCUMENTS 4,609,674 A * 9/1986 Gupte ........................... 514/547

* cited by examiner

*Primary Examiner* — Melenie McCormick
(74) *Attorney, Agent, or Firm* — Kirschstein, et al.

(57) ABSTRACT

Liquid medicaments incorporate about 1.0-3.0% active benzoyl peroxide (BP) by weight in substantially fully solubilized form, while being substantially free of acetone and other harsh, dermatologically undesirable solvents. The novel compositions are produced by (a) creating an emulsion or slurry of BP in an emollient, topically acceptable ester, and (b) dissolving the emulsion or slurry in absolute alcohol. The medicaments may be used in the treatment of BP-responsive skin conditions in mammals, e.g., acne vulgaris or rosacea. The novel medicaments may be dispensed directly to the affected skin area through the use of an applicator device comprising a fluid reservoir associated with a foam applicator tip, or via a spray dispenser, atomizer or pump spray.

10 Claims, 1 Drawing Sheet

LIQUID COMPOSITIONS CONTAINING SOLUBILIZED BENZOYL PEROXIDE, MEANS FOR APPLYING SAME AND METHODS OF TREATMENT USING SAME

CROSS REFERENCE TO RELATED APPLICATIONS

This application is a division of U.S. patent application Ser. No. 11/820,949, filed Jun. 21, 2007, now allowed.

BACKGROUND OF THE INVENTION

Acne vulgaris, or simply, acne, is a skin disease affecting 80% of the human population from 11 to 30 years of age; and, as such, is the most common skin disease in the United States. If not properly treated acne may continue into middle age, resulting in permanent scarring, disfigurement, as well as emotional problems. Although treatment options exist, effective treatment is becoming more difficult due to the emergence of systemic antibiotic-resistant strains of Propionibacterium acnes, the bacteria responsible for acne.

Resistance to traditional anti-acne antibiotics is reported to have risen from "extremely rare" in the mid-1980's to over 60% in 1996. It is now estimated that 1 in 4 acne patients are infected by acne strains resistant to at least one of the major systemic antibiotics traditionally used by dermatologists. Cooper, Med. J. Aust., 169:259-261 (1998).

Rosacea is a chronic dermatitis of the face, especially of the nose and cheeks, characterized by a red or rosy coloration caused by dilation of capillaries, and the appearance of acne-like pimples. This condition is also called "acne rosacea," and is caused by similar bacterial agents in the skin. Rosacea has similarly become more resistant to traditional antibiotic therapies in recent years.

Conventional topical therapies for acne, depending on the severity and extent of the disease, include treatment of the patient with one or more of the following therapeutic agents: (1) comedolytic agents, such as salicylic acid, tretinoin, adapalene, azelaic acid, and tazarotene; (2) bactericidal agents, such as benzoyl peroxide; (3) topical antibiotics, such as clindamycin, erythromycin and tetracycline; and (4) antimicrobial agents, such as sodium sulfacetamide and metronidazole, which can act as anti-inflammatories.

Topically applied benzoyl peroxide ("BP") is considered the drug agent of choice in the effort to eliminate resistant acne strains. BP is clinically superior to the antibiotics in its ability to kill acne bacteria while continuing to repress resistant strains. In addition, BP is highly lipophilic and concentrates itself inside the lipid-rich, sebaceous, skin follicles where its bacterial action specifically targets P. acnes; and, despite its continued use, it does not cause resistant strains to develop. In fact, BP was found to be more effective than either clindamycin or erythromycin in killing the bacteria responsible for causing acne. Leyden, Cutis, 67 (suppl. 2):5-7 (2001); Leyden et al., Am. J. Clin. Derm., 2(1):33-39 (2001).

While topical medicaments containing BP have been used for at least several decades as a treatment for acne and rosacea, the formulations containing BP have generally been restricted to creams, gels and high viscosity liquids or lotions wherein BP can be suspended either in a colloidal matrix or a slurry. Liquid BP formulations proposed in the art, e.g., in U.S. Pat. No. 6,740,330, contain substantial concentrations of solvents highly irritating and/or drying to the skin, e.g., acetone. Dermatologically safe, truly solubilized BP formulations have not been available in the prior art. Such liquid formulations are desirable to allow BP to be applied to the affected skin sites by, e.g., a dab-on sponge or foam-tipped applicator associated with a reservoir, both for convenience and comfort of use and to allow greater penetration of BP into the skin layers than is achieved with conventional creams and gels. With greater penetration, lower concentrations of BP can be used.

The problem in creating liquid BP formulations is that BP is virtually insoluble in water and most solvents that may be safely used in dermatological preparations and do not cause undue irritation. BP is most soluble in solvents which are unsuitable for application to the skin in substantial concentrations, e.g., acetone, ethers, benzene or chloroform, or in solvents wherein the BP is unstable and degrades rapidly, e.g., propylene glycol formulations of which also have an undesirable greasy feel. In fact it has been found that BP stability in hydric solvents bears an inverse relationship to its solubility, with the least stable formulations being those using hydric vehicles wherein BP is most soluble. Chellquist et al., Pharm. Res., 9:1341-1346 (1992). Indeed, Chellquist et al. recommend using suspension formulations of BP in vehicles that exhibit low BP solubility in order to decrease BP degradation and achieve stability.

Since BP is not soluble in many dermatologically safe vehicles, it must be micropulverized in order to reduce particle size even when the BP is formulated as a suspension in a gel or cream vehicle; otherwise, the user can feel the gritty texture of the BP when the cream or gel is applied to the skin. Furthermore, formulating BP in creams, gels or lotions sometimes requires heating of various phases after the BP is added. Such pulverization or shearing of dry BP particles or heating of BP in suspension is quite dangerous because BP is very unstable and potentially explosive when heated or stressed (and milling processes generate substantial heat as well). Many accidental explosions have been reported worldwide in the production, storage and handling of BP bulk material. As a result, BP raw material is typically supplied and packaged phlegmatized (desensitized) with water to make it safe to transport and use.

It has been found that relatively stable submicron emulsions of BP can be formulated using surfactant/co-surfactant/oil/water mixtures, e.g., ternary mixtures of Cremophor EL, glycerin, caprylic-capric triglycerides and water. Nielloud et al., Drug Devel. Ind. Pharm., 28:863-870 (2002). Such microemulsions, however, are viscous, and despite the submicron size of the BP particles, they still tend to deposit in and clog the pores or cells of a sponge or foam-tip applicator, eventually preventing the exit of the BP-containing emulsion from the reservoir.

Topical liquid medicaments containing true, stable solutions of BP in pharmaceutically effective concentrations are required.

BRIEF SUMMARY OF THE INVENTION

The present invention resides, briefly stated, among other things, in (a) liquid medicaments for topical use on human skin containing BP in substantially fully solubilized form, (b) methods of producing such liquid medicaments, (c) methods of treating acne, rosacea, and other BP-responsive skin conditions using such medicaments and (d) delivery devices or systems for administering such medicaments to the skin area to be treated.

The medicaments of the invention contain active BP in concentrations of about 1.0-3.0% (w/w), and preferably about 2.0-2.5%; about 1-35% of at least one emollient, topically acceptable ester; and about 60-90% absolute alcohol (ethanol, 200 proof). The novel medicaments are prepared by creating an emulsion or slurry of BP in the emollient ester, adding the BP emulsion to absolute alcohol, and mixing or stirring until a clear solution is obtained. Additional ingredients such as anti-inflammatories, comedolytic agents, counter-irritants, fragrances and the like may be added to the solution. The medicaments of the invention are substantially acetone-free.

The novel liquid medicaments can be dispensed using sponge or foam-tipped applicators having absorbent applicator tips associated with fluid reservoirs in which the medicaments are retained. The BP medicaments may be applied to the skin using such applicators to provide effective topical treatment of BP-responsive skin conditions, such as acne and rosacea.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE PREFERRED EMBODIMENTS

Figure 1:
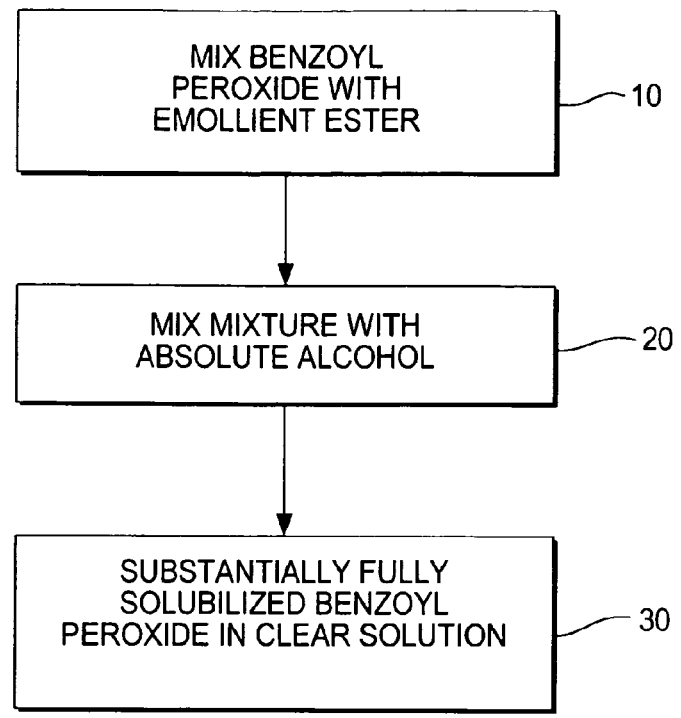
FIG. 1 is a block diagram depicting steps in a method of preparing a substantially fully solubilized BP in accordance with the invention.

The liquid medicaments of the present invention contain BP in substantially fully solubilized form while being substantially free of harsh or dermatologically undesirable solvents, e.g., acetone.

The novel medicaments comprise active BP in concentrations (w/w) from about 1.0% to about 3.0%, preferably about 2.0-2.5%; topically acceptable, emollient esters in concentrations (w/w) from about 5% to about 35%, and preferably from about 7.5% to about 30%; and absolute alcohol (200 proof) in concentrations (w/w) from about 60% to about 90%, and preferably from about 65% to about 88%. The liquid medicaments may also comprise from about 0% to about 5% water (w/w), preferably purified or distilled, and a total of about 0% to about 2% (w/w) topically safe and effective additives such as anti-inflammatories, comedolytic agents, counter-irritants and/or conventional additives such as fragrances, coloring agents or preservatives.

It has been discovered, surprisingly, that although the solubility of BP in absolute alcohol is poor, and is even poorer in alcohol/water mixtures, when an emulsion of BP is formed in a suitable emollient ester, e.g., an ester of caprylic/capric acid, that emulsions may be mixed with absolute alcohol (or even ethanol containing up to 5% water w/w) to form a clear, stable solution of BP. Although it is preferable to limit the amount of water in the medicaments of the invention, it has been found that up to 5% (w/w) of water may be included in these liquid medicaments without causing precipitation of BP in many cases.

The BP used in the novel medicaments is generally transported and stored phlegmatized with water. One such hydrous BP product is CADET® BPO-75W, supplied by Akzo Nobel (Chicago, Ill.), which is phlegmatized to a peroxide assay of about 75%-78%. The weight percentages given herein for "active BP" in the novel medicaments is the functional or active equivalent of phlegmatized BP. Thus, by way of illustration, 3.20% BP phlegmatized to a peroxide assay of about 78% would be equivalent to about 2.5% active or dry BP.

The topically acceptable, emollient esters used in the medicaments of the invention may be any esters in which a substantially homogeneous emulsion, suspension or slurry of BP can be formed and subsequently dissolved in absolute alcohol to form a clear solution. Preferred esters for use in the present invention include esters of caprylic/capric acid, e.g., pentaerythrityl tetracaprylate/tetracaprate or caprylic/capric triglyceride; esters of myristic acid, e.g., myreth-3-myristate; esters of benzoic acid, e.g., $C_{12}$-$C_{15}$ alkyl benzoate and esters of diheptanoic acid, e.g., PEG-4 diheptanoate. While an emulsion of BP in most of these esters readily forms a clear, stable solution in absolute alcohol, in the case of caprylic/capric triglyceride it may be necessary to add up to 5% water (by weight of the entire formulation) to achieve a stable solution.

The absolute alcohol used in the novel medicaments may be denatured with conventional denaturing agents known in the chemical art, e.g., phthalates such as diethyl phthalate.

Illustrative optional ingredients which may be used in the liquid medicaments of the present invention include comedolytic agents such as salicylic acid; anti-inflammatory agents such as tea tree oil (which also has topical antibacterial activity); soothing emollients such as comfrey extract; and counter-irritants, such as menthol and camphor. Any other conventional additives to liquid medicaments for topical use, including, but not limited to, coloring agents, fragrances and preservatives, may also be included. Preservatives are not generally required, though, because of the high alcohol content of the subject medicaments.

The medicaments of the invention may be prepared by any method known to those skilled in the arts of pharmaceutical or cosmetic formulations for achieving a clear, stable liquid solution containing the ingredients listed above, particularly the requisite concentration of active BP. Said solution must be safe to produce, store and use and be suitable for application to human skin for the treatment of BP-responsive skin conditions or disorders such as acne and rosacea. By one preferred method of preparation as illustrated in FIG. 11, the absolute alcohol is weighed into a main vessel equipped with a mixer and covered. The emollient ester or esters are then placed into a second vessel and the BP is added thereto with slow mixing, as depicted by step 10. The mixing or stirring of the alcohol in the main vessel is commenced and the blend of BP and ester is then added slowly thereto with continuous mixing, as depicted in step 20. The mixing in the main vessel is continued until a clear solution is achieved with no visible crystals, as depicted in step 30. Any optional ingredients are then added to the main vessel and the mixing is continued until a clear liquid is achieved.

One exemplary formulation of the novel medicaments prepared by the above procedure comprises by weight:

65.70% absolute alcohol
2.50% active BP (3.20% BP phlegmatized to peroxide assay of about 78%)
30.00% pentaerythrityl tetracaprylate/tetracaprate
0.50% tea tree oil
0.10% menthol
0.50% comfrey extract The novel medicaments exhibit good stability, with little degradation of the BP at storage temperatures of 25-50° C. While a small amount of water may be added in preparing the medicaments, it has been found that the presence of more than 5% water by weight adversely affects the solubility and stability of the BP active ingredient.

The substantially fully solubilized BP solution of the invention enable more clinically effective treatment of affected skin areas with lower concentrations of BP than in many prior art BP medicaments, and yet achieves better therapeutic results with less irritation.

The medicaments of the invention may be delivered, dispensed or applied to the skin area to be treated by any conventional means. For example, the liquid medicaments may be stored in conventional bottles, vials, plastic containers and the like, and applied to the skin by means of cotton balls, swabs, cotton tipped applicators, dermatological sponges or disposable wipes, or through the use of cloth pledgettes impregnated with of the medicaments and stored in sealed containers or pouches, such as disclosed in U.S. Pat. No. 6,740,330.

Figure 2:
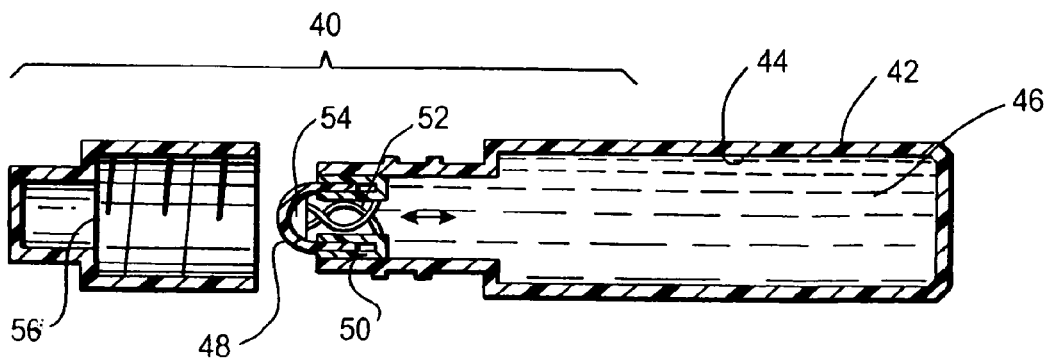
FIG. 2 is an exploded sectional view of an applicator for dispensing the fully solubilized BP to a patient.

One preferred delivery system or delivery device for the novel medicaments is an applicator, as depicted in FIG. 2, comprising an applicator housing 42 containing an internal fluid reservoir 44. The housing is preferably in the form of a hollow tube, vial, barrel, wand or other fluid-retaining container. The reservoir is in fluid communication with a porous applicator tip 48, through which the liquid medicament solution 46 contained in the reservoir can be dispensed.

The applicator housing may be rigid, such as a rigid plastic tube, or may be deformable, such as a thin-walled tube which may be squeezed to force the fluid in the reservoir onto the applicator tip The applicator tip 48 can be made of any fluid-absorbing, porous material, preferably in sheet form, suitable for temporarily retaining fluid absorbed from the reservoir and releasing said fluid upon being squeezed or pressed against a surface, such as the skin area intended to be treated. Suitable fluid-absorbing, porous materials include, for example, natural or synthetic sponges, synthetic foams such as polyester polyurethane foam, high or low density polyethylene, polypropylene homopolymer resins, nylon, or any other suitable absorbent, porous materials used in the pharmaceutical and cosmetic arts to apply liquids or other fluids to the skin.

In the applicator embodiment shown in FIG. 2, peripheral edges of the sheet material tip 48 are frictionally captured in an annular recess formed in a plug 50. A spring 52 having a bulbous head 54 is pressed against the inside sheet material tip 48. During dispensing when the tip 48 is pressed against the skin area to be treated, the spring 52 is compressed. After the dispensing is completed, the spring 52 returns to its initial position. The applicator housing may further comprise a hollow applicator neck in fluid communication with the solution in the reservoir, said neck being closed at its distal end by the applicator tip 48 mounted therein so that fluid may flow from the reservoir through the neck and permeate or "wet" the applicator tip. A sealing cover or cap 50 is preferably provided to fit over and encase the applicator tip when not in use. The sealing cover may be securely fitted to the applicator neck to provided a substantially airtight seal over the applicator tip by any standard means known in the container art, including by screwing the cover onto threads provided on the applicator neck or by causing the cover to engage the applicator neck by means of a friction fit, or snap action.

Suitable applicators for use in delivering or dispensing the medicaments of the invention are well-known in the fields of cosmetics and topical medicaments. Such applicators are used, for example, to dispense local anti-pruritic medication to pruritic skin areas, local anesthetics to painful skin areas, or antiseptic preparations used, e.g., to prepare a site for surgery. However, it has not previously been possible to effectively dispense BP-containing medicaments through such sponge or foam-tipped applicators because stable, solubilized liquid medicaments containing pharmaceutically effective concentrations of BP were not available. A liquid or fluid form of BP in which the active ingredient is not substantially fully solubilized may initially be dispensable from a typical foam-tipped applicator, but the applicator tip pores will eventually become clogged with BP crystals and residue, reducing fluid flow through the applicator tip to unacceptable levels. Moreover, even a liquid medicament containing initially a pharmaceutically acceptable concentration of BP is not ultimately useful in the topical treatment of acne if it is unstable and the BP rapidly degrades within a matter of days or weeks so that the effective concentration of BP in the medicaments falls below acceptable levels.

The novel BP medicaments of the invention can thus be delivered from a foam-tipped applicator, which contains or houses the liquid medicaments in a sealed reservoir, to a skin area suffering from a BP-responsive condition such as acne or rosacea. This delivery system provides a number of advantages over prior art means for delivering BP-containing medicaments. No separate means such as a cotton pad, ball or swab is required in order to apply the medicament, as is the case with conventional liquids or lotions containing BP which are stored in closed bottles, tubes and the like and which cannot pass through a foam or sponge applicator tip without causing clogging thereof. The foam-tipped applicator which may be used to deliver the novel medicaments can administer a more precise dosage to only the skin area desired to be treated, with better partition of the medicament from the applicator material than is the case with a cotton ball, swab or pledget, and with little likelihood of spillage or leakage. The applicator tip need only be covered, e.g., by a cap, and the applicator can be conveniently carried in a bag or pocket and be ready to use at a moment's notice.

Another preferred delivery system or delivery device for the novel medicament comprises a device suitable for dispensing a spray or mist of the liquid benzoyl peroxide solution, such as a spray container, an atomizer, a pump spray and the like, having a reservoir filled with the liquid BP medicament. The substantially fully solubilized BP of the invention is suitable for dispensing by spray means from said reservoir without clogging the hole in the spray nozzle or tube or the spray exit hole, unlike prior art BP lotions, gels, creams, partial solutions or unstable solutions wherein particles of BP readily precipitated. Such a spray or mist of the BP solution according to the invention can be applied advantageously to hairy area of the scalp and body, the skin of which frequently develops BP-responsive skin conditions. The BP spray or mist can also be readily applied to hard-to reach areas of the body, such as the back, which(without the assistance of another person, could rarely be treated conveniently with prior art medicaments and applicators.

Thus, the present invention also comprehends a novel method of treating BP-responsive skin conditions on a skin area of a patient, said method comprising the direct application of a liquid medicament containing a pharmaceutically effective amount of BP to the skin area by means of a foam-tipped applicator associated with a fluid reservoir containing the liquid medicament, or by dispensing a spray or mist of BP solution to the affected skin area from a spray container, atomizer, pump bottle or any other known means for dispensing sprays or mists. Said method also comprises treating BP-responsive skin conditions on a skin area of a patient by applying to said skin area a liquid medicament for topical use on human skin containing substantially fully solubilized benzoyl peroxide (BP), said medicament being substantially free of acetone, ethers, benzene and chloroform.

The invention further comprehends a method of treating BP-responsive skin conditions on a skin area of a patient, said method comprising the application to the area of a liquid medicament containing substantially fully solubilized BP in an alcoholic vehicle. This method of treatment enables the use of lower concentrations of BP with better penetration of the affected skin layers than that achieved by conventional BP creams, gels or liquids. The lower concentrations of BP that can be used decrease skin irritation, and the addition of emollient esters to the novel medicaments used in the method of treatment, help to further reduce irritation and inflammation.

The following examples provide detailed illustrations of liquid medicaments according to preferred embodiments of the present invention, methods of producing the same, and the results of the solubility and stability testing on these medicaments. These examples are not intended, however, to limit or restrict the scope of the invention in any way, and should not be construed as providing methods, conditions, ingredients or starting materials which must be utilized exclusively to practice the present invention.

EXAMPLES 1-24

The following ingredients and procedures were used to prepare and assess the liquid medicaments whose formulations are set forth in Tables I through IV:

Ingredients:
Absolute Alcohol SD29C (200 proof alcohol denatured with diethyl phthalate,
Pharmco/Aaper, Shelbyville, Ky.)
Benzoyl Peroxide L-W78 (Axzo Nobel, Chicago, Ill.)
LIPONATE® Emollient Esters (Lipo Chemical Co., Paterson, N.J.)
Salicylic Acid
Tea Tree Oil
Menthol
Comfrey Extract Procedures:
The absolute alcohol was weighed out into a clean main vessel equipped with an overhead mixer and propeller blade. The main vessel was immediately covered. The emollient ester was then added to a second clean vessel equipped with an overhead blender and mixed at slow speed. The BP was added gradually to the ester in the second vessel, and slow mixing continued until the BP was thoroughly "wet out."

The main vessel was uncovered and mixing of the alcohol began. The blend of ester and BP was added slowly to the alcohol in the main vessel while mixing. The mixing continued until the BP was fully dissolved and no crystals were visible.

The optional ingredients, tea tree oil, menthol and comfrey extract, were next added to the BP blend in the main vessel. Mixing was continued until a clear liquid was obtained.

Each batch of liquid product was allowed to stand in a clear container and visually examined initially and again after 24 hours for clarity, crystal formation, settling of solids, and so forth. The results of these observations are set forth in Tables I-IV.

Samples of each batch of liquid product were placed in sealed containers and allowed to stand for four weeks at controlled temperatures of either 25° C. or 50° C. After each one week interval the samples were tested to assess the stability of the BP active ingredient. The results of these tests, reported simply as "stable" or "not stable," are set forth in Tables I-IV.

In Tables I-IV, the quantities of BP stated in each formulation are of "active" BP.

The LIPONATE® emollient esters (Lipo Chemical Co., Paterson, N.J.) identified in Tables I-IV below include the following:

| PRODUCT NAME | INCI NAME |
| --- | --- |
| Liponate ® GC | Caprylic/Capric Triglyceride |
| Liponate ® NEB | C12-15 Alkyl Benzoate |
| Liponate ® 143-M | Myreth-3 Myristate |
| Liponate ® 2-DH | PEG-4 Diheptanoate |
| Liponate ® NPGC-2 | Neopentyl Glycol Dicaprylate/Dicaprate |
| Liponate ® PE-810 | Pentaerythrityl Tetracaprylate/Tetracaprate |

Of the medicament formulations are reflected in Tables I-IV below, the formulations of Examples 2-4, 6, 12-14, 16-19, and 21-24 come within the scope of the present invention. All of these formulations resulted in clear stable solutions of BP Examples 1, 5, 7-11, 15 and 20 are presented for purposes of experiential comparison. These formulations resulted in either non-fully solubilized BP and/or immediate or eventual precipitation of BP crystals within the study period.

TABLE I

Formulations Without Water

| INGREDIENTS | Example 1 | Example 2 | Example 3 | Example 4 | Example 5 | Example 6 |
| --- | --- | --- | --- | --- | --- | --- |
| A. Benzoyl Peroxide L-W78 | 2.00 g | 2.00 g | 2.00 g | 2.00 g | 2.00 g | 2.00 g |
| Liponate GC | 8.50 g | | | | | |
| Liponate NEB | | 8.50 g | | | | |
| Liponate 143-M | | | 8.50 g | | | |
| Liponate 2-DH | | | | 8.50 g | | |
| Liponate NPGC-2 | | | | | 8.50 g | |
| Liponate PE-810 Liponate | | | | | | 8.50 g |
| B. Salicylic Acid | 0.75 g | 0.75 g | 0.75 g | 0.75 g | 0.75 g | 0.75 g |
| Alcohol 200 proof | 87.65 g | 87.65 g | 87.65 g | 87.65 g | 87.65 g | 87.65 g |
| Tea Tree Oil | 0.50 g | 0.50 g | 0.50 g | 0.50 g | 0.50 g | 0.50 g |
| Menthol | 0.10 g | 0.10 g | 0.10 g | 0.10 g | 0.10 g | 0.10 g |
| Comfrey Extract | 0.50 g | 0.50 g | 0.50 g | 0.50 g | 0.50 g | 0.50 g |
| Initial R.T. observation | B.P. Crystal formation | Clear liquid | Clear liquid | Clear liquid | B.P settled to bottom | Clear liquid |
| 24 hr. observation | B.P. Crystal formation | Clear liquid | Clear liquid | Clear liquid | B.P settled to bottom | Clear liquid |

TABLE I-continued

Formulations Without Water

| INGREDIENTS | Example 1 | Example 2 | Example 3 | Example 4 | Example 5 | Example 6 |
|---|---|---|---|---|---|---|
| Stability Test: | 1 week | 1 week | 1 week | 1 week | 1 week | 1 week |
| 25 c stability | x | stable | stable | stable | x | stable |
| 50 c stability | x | stable | stable | stable | x | stable |
|  | 2 weeks | 2 weeks | 2 weeks | 2 weeks | 2 weeks | 2 weeks |
| 25 c stability | x | stable | stable | stable | x | stable |
| 50 c stability | x | stable | stable | stable | x | stable |
|  | 3 weeks | 3 weeks | 3 weeks | 3 weeks | 3 weeks | 3 weeks |
| 25 c stability | x | stable | stable | stable | x | stable |
| 50 c stability | x | stable | stable | stable | x | stable |
|  | 4 weeks | 4 weeks | 4 weeks | 4 weeks | 4 weeks | 4 weeks |
| 25 c stability | x | stable | stable | stable | x | stable |
| 50 c stability | x | stable | stable | stable | x | stable |

TABLE II

Formulations with Water

| INGREDIENTS | Example 7 | Example 8 | Example 9 | Example 10 | Example 11 | Example 12 | Example 13 | Example 14 | Example 15 |
|---|---|---|---|---|---|---|---|---|---|
| A. Benzoyl Peroxide L-W78 | 2.00 g | 2.00 g | 2.00 g | 2.00 g | 2.00 g | 2.00 g | 2.00 g | 2.00 g | 2.00 g |
| Liponate GC | 8.50 g |  |  |  |  |  | 8.50 g |  |  |
| Liponate NEB |  | 8.50 g |  |  |  |  |  | 8.50 g |  |
| Liponate 143-M |  |  | 8.50 g |  |  |  |  |  |  |
| Liponate 2-DH |  |  |  | 8.50 g |  |  |  |  |  |
| Liponate NPGC-2 |  |  |  |  | 8.50 g |  |  |  | 8.50 g |
| Liponate PE-810 |  |  |  |  |  | 8.50 g |  |  |  |
| Liponate |  |  |  |  |  |  |  |  |  |
| B. Salicylic Acid | 0.75 g | 0.75 g | 0.75 g | 0.75 g | 0.75 g | 0.75 g | 0.75 g | 0.75 g | 0.75 g |
| Alcohol 200 proof | 87.65 g | 87.65 g | 87.65 g | 87.65 g | 87.65 g | 82.65 g | 82.65 g | 82.65 g | 82.65 g |
| Tea Tree Oil (0.50) | ~ | ~ | ~ | ~ | ~ | 0.50 | 0.50 | 0.50 | 0.50 |
| Menthol | 0.10 g | 0.10 g | 0.10 g | 0.10 g | 0.10 g | 0.10 g | 0.10 g | 0.10 g | 0.10 g |
| Comfrey Extract | 0.50 g | 0.50 g | 0.50 g | 0.50 g | 0.50 g | 0.50 g | 0.50 g | 0.50 g | 0.50 g |
| C. DI Water | 15.00 g | 10.00 g | 5.00 g | 5.00 g | 10.00 g | 5.00 g | 5.00 g | 5.00 g | 5.00 g |
| Initial R.T. observation | Clear liquid crystals on bottom | Clear liquid | Clear liquid | Cloudy liquid. Crystals on bottom | Cloudy liquid Crystals on bottom | Clear liquid | Clear liquid | Clear liquid | Cloudy liquid |
| 24 hr. observation | No change | Cloudy liquid | Hazy liquid | No change | No change | Clear liquid | Clear liquid | Clear liquid | No change |
| Stability Test: | 1 week | 1 week | 1 week | 1 week | 1 week | 1 week | 1 week | 1 week | 1 week |
| 25 c stability | No change | No change | No change | No change | No change | Clear liquid | Clear liquid | Clear liquid | Cloudy liquid |
| 50 c stability | No change | No change | No change | No change | No change | Stable | Stable | Stable | B.P on bottom |
|  | 2 weeks | 2 weeks | 2 weeks | 2 weeks | 2 weeks | 2 weeks | 2 weeks | 2 weeks | 2 weeks |
| 25 c stability | x | x | x | x | x | Stable | Stable | Stable | Not stable |
| 50 c stability | x | x | x | x | x | Stable | Stable | Stable | Not Stable |
|  | 3 weeks | 3 weeks | 3 weeks | 3 weeks | 3 weeks | 3 weeks | 3 weeks | 3 weeks | 3 weeks |
| 25 c stability | x | x | x | x | x | Stable | Stable | Stable | x |
| 50 c stability | x | x | x | x | x | Stable | Stable | Stable | x |

TABLE II-continued

Formulations with Water

| INGREDIENTS | Example 7 | Example 8 | Example 9 | Example 10 | Example 11 | Example 12 | Example 13 | Example 14 | Example 15 |
|---|---|---|---|---|---|---|---|---|---|
| | 4 weeks | 4 weeks | 4 weeks | 4 weeks | 4 weeks | 4 weeks | 4 weeks | 4 weeks | 4 weeks |
| 25 c stability | x | x | x | x | x | Stable | Stable | Stable | x |
| 50 c stability | x | x | x | x | x | Stable | Stable | Stable | x |

TABLE III

Varying Concentrations of Emollient Ester

| INGREDIENTS | Example 16 | Example 17 | Example 18 | Example 19 | Example 20 |
|---|---|---|---|---|---|
| A. Benzoyl Peroxide L-W78 | 2.00 g | 2.00 g | 2.00 g | 2.00 g | 2.00 g |
| Liponate GC | | | | | |
| Liponate NEB | 15.00 g | 20.00 g | 25.00 g | 30.00 g | 50.00 g |
| Liponate 143-M | | | | | |
| Liponate 2-DH | | | | | |
| Liponate NPGC-2 | | | | | |
| Liponate PE-810 | | | | | |
| Liponate | | | | | |
| B. Salicylic Acid | 0.75 g | 0.75 g | 0.75 g | 0.75 g | 0.75 g |
| Alcohol 200 proof | 81.15 g | 76.15 g | 71.15 g | 66.15 g | 46.15 g |
| Tea Tree Oil | 0.50 g | 0.50 g | 0.50 g | 0.50 g | 0.50 g |
| Menthol | 0.10 g | 0.10 g | 0.10 g | 0.10 g | 0.10 g |
| Comfrey Extract | 0.50 g | 0.50 g | 0.50 g | 0.50 g | 0.50 g |
| Initial R.T. observation | Clear liquid | Clear liquid | Clear liquid | Clear liquid | Too oily on skin, clear. |
| 24 hr. observation | Clear liquid | Clear liquid | Clear liquid | Clear liquid | Clear liquid |
| Stability Test: | 1 week | 1 week | 1 week | 1 week | 1 week |
| 25 c stability | Stable | Stable | Stable | Stable | Stable |
| 50 c stability | Stable | Stable | Stable | Stable | Stable |
| | 2 weeks | 2 weeks | 2 weeks | 2 weeks | 2 weeks |
| 25 c stability | Stable | Stable | Stable | Stable | Stable |
| 50 c stability | Stable | Stable | Stable | Stable | Stable |
| | 3 weeks | 3 weeks | 3 weeks | 3 weeks | 3 weeks |
| 25 c stability | Stable | Stable | Stable | Stable | Stable |
| 50 c stability | Stable | Stable | Stable | Stable | Stable |
| | 4 weeks | 4 weeks | 4 weeks | 4 weeks | 4 weeks |
| 25 c stability | Stable | Stable | Stable | Stable | Stable |
| 50 c stability | Stable | Stable | Stable | Stable | Stable |

TABLE IV

Various Esters at 30% (w/w)

| INGREDIENTS | Example 21 | Example 22 | Example 23 | Example 24 |
|---|---|---|---|---|
| A. Benzoyl Peroxide L-W78 | 2.00 g | 2.00 g | 2.00 g | 2.00 g |
| Liponate GC | | | | |
| Liponate NEB | 30.00 g | | | |
| Liponate 143-M | | 30.00 g | | |
| Liponate 2-DH | | | 30.00 g | |
| Liponate NPGC-2 | | | | |
| Liponate PE-810 | | | | 30.00 g |
| Liponate | | | | |
| B. Salicylic Acid | 0.75 g | 0.75 g | 0.75 g | 0.75 g |
| Alcohol 200 proof | 66.15 g | 66.15 g | 66.15 g | 66.15 g |
| Tea Tree Oil | 0.50 g | 0.50 g | 0.50 g | 0.50 g |
| Menthol | 0.10 g | 0.10 g | 0.10 g | 0.10 g |
| Comfrey Extract | 0.50 g | 0.50 g | 0.50 g | 0.50 g |
| Initial R.T. observation | Stable | Stable | Stable | Stable |
| 24 hr. observation | Stable | Stable | Stable | Stable |
| Stability Test: | 1 week | 1 week | 1 week | 1 week |
| 25 c stability | Stable | Stable | Stable | Stable |
| 50 c stability | Stable | Stable | Stable | Stable |

TABLE IV-continued

Various Esters at 30% (w/w)

| INGREDIENTS | Example 21 | Example 22 | Example 23 | Example 24 |
|---|---|---|---|---|
| | 2 weeks | 2 weeks | 2 weeks | 2 weeks |
| 25 c stability | Stable | Stable | Stable | Stable |
| 50 c stability | Stable | Stable | Stable | Stable |
| | 3 weeks | 3 weeks | 3 weeks | 3 weeks |
| 25 c stability | Stable | Stable | Stable | Stable |
| 50 c stability | Stable | Stable | Stable | Stable |
| | 4 weeks | 4 weeks | 4 weeks | 4 weeks |
| 25 c stability | Stable | Stable | Stable | Stable |
| 50 c stability | Stable | Stable | Stable | Stable |

It will thus be shown that there are provided compositions, methods and delivery devices or systems which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

I claim:

1. A method of treating benzoyl peroxide (BP) responsive conditions on a skin area of a patient in need thereof, said method comprising the step of: applying a pharmaceutically effective amount of a clear liquid solution of benzoyl peroxide to the skin area using a foam-tipped applicator, wherein said clear liquid solution of BP comprises benzoyl peroxide, absolute alcohol and an ester selected from the group consisting of pentaerythrityl tetracaprylate/tetracaprate, myrethy-3-myristate and PEG-4diheptanoate and wherein said solution is substantially free of acetone, ethers, benzene and chloroform.

2. A method of treating benzoyl peroxide (BP) responsive conditions on a skin area of a patient in need thereof, said method comprising the step of: applying a spray or mist of a pharmaceutically effective amount of a clear liquid solution of BP to the skin area using a spray container, an atomizer or a spray pump, wherein said clear liquid solution of BP comprises benzoyl peroxide, absolute alcohol and an ester selected from the group consisting of pentaerythrityl tetracaprylate/tetracaprate, myrethy-3-myristate and PEG-4 diheptanoate and wherein said solution is substantially free of acetone, ethers, benzene and chloroform.

3. The method according to claims 1 or 2, wherein said liquid medicament comprises about 1.0%-3.0% (w/w) active BP.

4. The method according to claims 1 or 2, wherein said liquid medicament comprises about 60%-90% (w/w) absolute alcohol.

5. The method according to claims 1 or 2, wherein said liquid medicament comprises about 5%-35% (w/w) of said ester.

6. The method according to claims 1 or 2, wherein said ester is pentaerythrityl tetracaprylate/tetracaprate.

7. The method according to claims 1 or 2, wherein said clear liquid solution of BP additionally comprises about 0%-5% water (w/w).

8. The method according to claims 1 or 2, wherein said clear liquid solution of BP additionally comprises 0%-2% (w/w) of tea tree oil, menthol or comfrey extract.

9. The method according to claims 1 or 2, wherein said BP is phlegmatized with water.

10. The method according to claims 1 or 2, wherein said skin area is a hairy area of the scalp or body.

* * * * *